(12) United States Patent
Xin

(10) Patent No.: US 6,916,845 B2
(45) Date of Patent: Jul. 12, 2005

(54) METHOD FOR PREVENTION AND TREATMENT OF MALE AND FEMALE SEXUAL DYSFUNCTION

(76) Inventor: Zhongcheng Xin, No. 8 Xishiku St., Beijing, 100034 (CN)

( * ) Notice: Subject to any disclaimer, the term of this patent is extended or adjusted under 35 U.S.C. 154(b) by 0 days.

(21) Appl. No.: 10/228,346

(22) Filed: Aug. 26, 2002

(65) Prior Publication Data

US 2003/0153515 A1 Aug. 14, 2003

Related U.S. Application Data

(60) Continuation-in-part of application No. 09/859,910, filed on May 17, 2001, now abandoned, which is a division of application No. 09/596,109, filed on Jun. 16, 2000, now abandoned.

(30) Foreign Application Priority Data

Jun. 17, 1999 (KR) ......................................... 1999-22665

(51) Int. Cl.⁷ .............................................. A61K 31/35
(52) U.S. Cl. ....................................................... 514/456
(58) Field of Search ........................................... 514/456

(56) References Cited

U.S. PATENT DOCUMENTS 5,731,339 A * 3/1998 Lowrey ...................... 514/400

OTHER PUBLICATIONS

STRENIXX–Male Potency Formula, as advertised on the internet, www.sterinexx.com According to Trademark Electroni Search System this product has been in commerce since 1992.*

* cited by examiner

*Primary Examiner*—San-Ming Hui
(74) *Attorney, Agent, or Firm*—Thorpe North & Western, LLP

(57) ABSTRACT

The present invention relates to a method of the prevention or treatment of sexual dysfunction in a male or a female patient comprising administrating to said patient a prevention or treatment amount of icariin or a pharmaceutical composition containing an effective amount of icariin.

3 Claims, No Drawings

METHOD FOR PREVENTION AND TREATMENT OF MALE AND FEMALE SEXUAL DYSFUNCTION

This application is a continuation-in-part of application Ser. No. 09/859,910 filed May 17, 2001 now abandoned which is a divisional application Ser. No. 09/596,109 filed Jun. 16, 2000 abandoned.

FIELD OF INVENTION

The present invention is the continuation-in-part application based on U.S. Patent Application Ser. No. 09/859,910 filed May 17, 2001, which is a divisional of U.S. Application Ser. No. 09/596,109 filed Jun. 16, 2000, which is from Korean Pat. Appl'n. No. KR99-22665 filed Jun. 17, 1999, and relates to a method of the prevention or treatment of a male and female sexual dysfunction which comprising administrating a prevention or treatment amount of icariin or a pharmaceutical composition containing icariin to a patient who needs.

BACKGROUND OF INVENTION

Both of male and female sexual function are similarity includes sexual desire or libido, arousal with penile erection and clitoris engorgement and vaginal lubrication, ejaculation and orgasm phases. Both of male and female sexual dysfunction is a trouble in any one of these function can result from neurogenic disorder, sexual organ vasculargenic disorder, hormongenic disorder and sexual organ pathophysionlogic changes induced by trauma include pubic bone fracture and spinal cord injury and systematic disease such as diabetics or hypertension and taking drugs. Drug induced sexual dysfunction has been proposed as a common pathophysiologic entity and a more than 25% incidence drug-associated sexual dysfunction in a medical outpatient population. Vasodilator, however, have no in relevant to effects on sexual function and even produce an adverse effect on formal sexual function, such as Seagraves et al (Erectile dysfunction associated with pharmacological agents. In: Segraves RT, Schoenberg HW, eds. Diagnosis and Treatment of Erectile Disturbances. New York: Plenum, 1985: 22) and Horowitz and Gobel (Drugs and impaired male sexual function Drugs 18;206, 1979) noted that sexual dysfunction has been associated with virtually every available vasodilator such as antihypertensive agent include that alpha-methyldopa 20–30%, guanethidine 24%, clodidine 41%, reserpine 30–40%, propranolol 13.8%, bendrofluazide 36% of patients and these results indicated that sexual function is special hemodinamic changes in sexual organ and very different from systematic hemodinamic procedure and the most of vasodilator may decrease sexual organ blood perfusion, therefore, induce adverse effects on sexual function.

Clinically sexual dysfunction in male can classify to decreased sexual desire or libido, erectile dysfunction, ejaculatory dysfunction and orgasm disorder, In female also classified to sexual arousal disorder include difficult achieve clitoris engorgement and vaginal lubrication, and orgasm disorder. Frequently, more than one of these problems presents themselves simultaneously.

Sexual dysfunction has been classified to psychogenic disorder and organic disorder. Due to recent progress in diagnostic methods, studies indicated that there are more than 50% of patients found organic disease. According to statistics, it has been reported that the incidences of male and/or female sexual dysfunction was approximately 50% of adults aged 40–70 years old and it is significantly increased by aging.

Traditionally, management of sexual dysfunction based on psychological consultation and tonic drugs and/or tried to use vasodilator attempt to treating sexual dysfunction. However, the succession ratio was very poor. A few of agents which has vasodilating effect such as papaverine, phentolamine and prostaglandine El are only used locally by intra-cavemosal injection therapy clinically. However, these agents are restrictedly used because of frequency of undesirable side effects including lowering systematic blood press, pain, prolonged erection such as priapism and penile fibrosis, and it is difficult used as an oral administration.

Recently, scientists demonstrate the detailed special structure of sexual organ of corpus cavernosum(CC) in male and clitoris in female, which is like a closed cylinder surrounded by outline with connective tissue membrane tunica albuginea and the inside contains special erectile tissue CC which consist of special smooth muscle, collagen and elastin, and linked by associate arteries, veins and nerves. The mechanism of regulation smooth muscle tone in CC is very different from systematic blood vessels, and there are specially distributed non-adrenalin non-cholinergic (NANC) nerve terminal which synthesis and release nitric oxide(NO) and phosphodiesterase type V(PDE5) which specially distributed in sexual organ plays the most important role in regulation of sexual function.

Sexual activity is a special hemodynamic procedure in sexual organ which mediated by relaxation of CC smooth muscle and its associated arterioles to increase blood flow into CC and reduce vein leakage to induce penile erection or clitoris engorgement. Such a sexual function is mediated by neuro-endocrinery regulation. During sexual stimulation, non-adrenalergic non cholenergic(NANC) nerve terminal which is specially distributed on CC, synthesis and release nitric oxide(NO) by NO synthesis(NOS), NO increased cGMP levels induce relaxation smooth muscle of CC and associate arteries, increase CC blood flow to induce penile erection or clitoris engorgement. cGMP which is the most important molecular can hydrolytic breakdown by cGMP specific phosphodiesterase V(PDE5) and loss its activity. So, NO-cGMP signaling pathway plays the important key role in regulation of sexual function. This important discovery in molecular biological researches demonstrated that among of the molecular which plays the most important role of regulating sexual function are included nitric oxide(NO), nitric oxide synthssis(NOS), gunylate cyclase(GC) and CGMP and PDE5. Agent, therefore, which has specific inhibiting effect on PDE5 activity to increase CC cGMP levels can be used for oral medication to treatment of sexual dysfunction with or without systematic side effects.

Recent study demonstrated that PDE5 is specifically distributed in CC compared to systematic blood vessels and other organs(the ratio is more than 10000 times) and PDE5 specific inhibitor such as Sildenafil can block cGMP hydrolysis to increase cGMP levels for using oral medication for treating sexual dysfunction in clinically. Sildenafil however, merely induces a transient erection by using a chemical agent, are too expensive and may cause undesirable systematic side effects including flashing, headache, cardiac problem and visional problem. Therefore, uses such a transient therapy is also restricted clinically.

Ideal drug for treating sexual dysfunction should be as an oral administration and have the specific action on sexual organ to enhancing sexual activity and safe and no or minimal of systematic side effects and have the long-term therapeutic activity. Recent studies have taken a growing interest in search a therapeutic agent for sexual dysfunction more focus on NO-cGMP specific PDE5 inhibitor for specific action on sexual organ to reduce systematic side effects.

Icariin is isolated from natural plant *Epimedii herba*, which is as a standard compound used for drug analysis only by now, a few studies reports the effects of icariin on enhancing immunomodulating effect, anti-hepatotoxic, anti-fatigue, prevention of aging and mild vasodilating activities. However, no any effects of icariin for enhancing sexual function has been reported.

DISCLOSING OF INVENTION

The present inventor has extensively investigated the available literatures and has continuously conducted studies and experiments related to overcome the problem of sexual dysfunction. As a result, it has been found that icariin, isolated from a certain *Epimedii herba* has a strong specific relaxation effect on corpus cavernosm of penis and clitoris to enhancement of sexual function. The pharmaceutical mechanism studies found that icariin is a new PDE5 inhibitor can enhance sexual function and it is mediated by enhancement of the activity of NO-cGMP signaling pathway in CC of penis and clitoris and by inhibit CGMP specific PDE5 activity, and thus can be effectively and safely used as medical agent for long-term preventing and treating a sexual dysfunction. The present invention is finished based on such discovery.

DETAILED DESCRIPTION OF INVENTION

The present invention relates to a method of the prevention or treatment of sexual dysfunction in male and female, which comprising administration a effective prevention or treatment amount of icariin or pharmaceutical composition containing icariin to a patient who needs.

The present invention also relates to a use of icariin ($C_{33}H_{40}O_{15}$, molecular weight: 676.67) for the manufacture of pharmaceutical for the prevention or treatment of sexual dysfunction in male and female.

The Icariin is a floavonoid isolated from *Epimedii herba*. *Epimedii herba* contains many other components such as magnoflorine, querectin, epimedin A, B and C and which were detected by HPLC analysis. Among of these components of *Epimedii herba*, icariin is a new PDE5 inhibitor, it can increase cGMP levels in sexual organ to enhancing activity of NO-cGMP signaling pathway for inducing specific relaxation of CC smooth muscle of penis and clitoris to enhancing sexual potency, and it is the most effective component for preventing and treating sexual function of male and female.

The present invention relates the pharmaceutical composition according to the invention may be formulated from a conventional method by mixing icariin as an active component with a pharmaceutically acceptable carrier or a excipient such as starch, lactose, organic solvent and the like, and it can be administered in amount of from 1–1000 mg per dose. The dosage containing icariin includes tablet, pill, capsules, granular, dispersions, ointment, solution, patch, cream, form. The preferable route of administration includes oral, intramuscularly, and any other convenient mode of administration may be used. The icariin compound is advantageously administered 1–4 times per day.

Following examples and experiments will more specifically illustrate the present invention. However, it should be understood that the present invention is not limited by examples in any manner.

EXPERIMENT 1

Isolation of Icariin from *Epimedii herba*

Dried aerial parts of *Epidemic herb* was extracted 3 times with ethanol, an ethanol extract was obtained after removal of the solvent in vacuum. The ethanol extract was then suspended in water and put into D 101 resin column, cluted with different concentration of ethanol(from 30%–70%), according to TCL analysis collected icariin rich solution and evaporated the collected icariin rich fraction (contain icaiin 50% according to HPLC analysis). The Icariin rich fraction after evaporating was put into silica gel column and eluted with different ratio of MeOH and $CHCl_3$(1:8–1:4), isolated Icariin and purified it by repeated re-crystallization with ethanol. It has been shown the following data; amorphous yellow powder(Rf=0.23[solvent system of $CHCl_3$:McOH was used as the developer], M.P: 231–233° C.). HPLC analysis showed that the purity of pured Icariin is 98.8%.

EXPERIMENT 2

Safety Test

To investigate an acute toxicity of icariin, icariin was administered to SD rat. Total of 50 rats divide into 5 groups randomly and each group included 5 male and 5 female rats, respectively. The maximum dosage group for 3.0 g/kg, medium dosage group for 2.0 g/kg, sub-medium group for 1.0 g/kg and the minimum dosage group for 0.5 g/kg and comparative group for physiological saline solution only. Each of the drugs was once administered subcutaneously. After 7 days, it was shown that LDso of male was 1.88 g/kg and female was 1.96 g/kg. These results confirm that icariin has a low toxicity.

EXPERIMENT 3

Background of Efficacy Study

Penile erection is a specific hemodynamic process involving relaxation of smooth muscle of the CC and its associated arterioles. This relaxation process results in an increased flow of blood into the trabecular spaces of the CC. The process is generally accepted to be under the neuro-regulatory control and involves specific distributed in CC of non-adrenergic non-cholinergic (NANC) neuroeffector system. The search for the elusive agent of penile erection has recently led to nitric oxide(NO), a gaseous messenger molecule. NO, which during sexual stimulation is synthesized by nerve terminal of NANC neurons in the CC and also synthesized by endothelial cells lining sexual organ arteries and lucanar spaces of CC, plays the important role in mediating smooth muscle relaxation. NO activates the guanylate cyclase resulting in an increased conversion of guanosine triphosphate (GTP) to cyclic guanosine monophosphate (cGMP). cGMP provides the signal, which leads to relaxation of smooth muscle of the CC and penile arterioles. The level of cGMP is regulated through the balance between the rate of synthesis by guanylate cyclase and the rate of hydrolytic breakdown to 5☐-monophosphate (GMP) by cyclic nucleotide phosphodiesterase (PDE5). Therefore, agents that interdiction cGMP hydrolysis may increase the cGMP levels could be expected to enhance relaxation of smooth muscle in the CC and thereby facilitate penile erectile responses and clitoris engorgement to improve sexual function.

As the physiology of penile erection has been elucidated clearly, substances, which have the specific relaxation effects on CC to increase intracavemosal blood flow have been used for treating erectile dysfunction.

EXPERIMENT 4

Relaxation Effects of Icariin on CC of Rabbit

In order to understand the effects of Icariin on sexual function, we investigated the relaxation effects of Icariin on rabbit's CC smooth muscle in vitro, which can increase intracavernosal blood press (ICP) to enhance Sexal function and the other components of *Epimedii herba* include magnoflorine, querectin, epimedin A, B and C as the controls.

Sixty adults male New Zealand white rabbits(Weight: 2.5–3.0 kg) were used. Rabbits were anesthesia with sodium pentobarbital(50 mg/kg), penis was removed and corpus cavernous tissue were carefully isolated and made into 2×2×6 mm muscle strips for isometric tension was measured in organ chamber in vitro study with polygraph(MP 100 WS:Biopac systems, USA). CC muscle strip was fixed in 10 ml organ chamber containing Tyrode solution and continuously supplied with mixed gas(95% $O_2$ and 5% $CO_2$) and keep temperature at 37° C. The initial resting tensions of muscle strips were set at 2 g and tissue was allowed to equilibrate for 1.5–3.0 hours. Sub-maximal contractile responses to phenylepherine(PHE 5×10-6 M) were observed and optimal isometric tension was determined. To evaluate the relaxation effects of icariin (the other components magnoflorine, querectin, epimedin A, B and C as the controls) on CC muscle strips, investigated the relaxation effects of different dosage of icariin on muscle strips pre-contracted by PHE. And to investigate the pharmaceutical action mechanism, the effects of nitric oxide scavenger Nω-nitric-L-arginine(L-NNA), guanylate cyclase antagonist methylene blue and pyrogallol, soluble guanylate cyclase inhibitor 1H-[1,2,4]oxadiazolo[4,3,-a]quinoxalin-1-one (ODQ) on the relaxation effects of icariin on CC.

In the results, icariin showed a dose related relaxation effects on PDE induced pre-contracted CC muscle strips ($10^{-7}$ M: 0.08±0.04%, $10^{-6}$ M: 1.23±0.82%, $10^{-5}$ M: 4.42±1.08%, $10^{-4}$ M: 12±1.36% respectively.

$p<0.001$). The EC50 of icariin on the relaxation effects of CC smooth muscle was $4.67\times10^{-4}$ M. However, the other components include components magnoflorine, querectin, epimedin A, B and C showed had no significant relaxation effects on CC. The relaxation effects of icariin on CC smooth muscle were significantly inhibited by pre-treatment with nitric oxide scavenger L-NNA, guanylate cyclase antagonist methylene blue and pyrogallol, soluble guanylate cyclase inhibitor ODQ.

TABLE 1

The relaxation effects of icariin on PDE induced corpus cavernosum smooth muscle strips od rabbit.

| Icariin conc. | $10^{-6}$ M | $10^{-5}$ M | $10^{-4}$ M | p value |
|---|---|---|---|---|
| Control (n = 8) | 1.23 ± 0.82% | 4.42 ± 1.08% | 23.12 ± 1.36% | <0.01 |

TABLE 2

Inhibiting responses of nitric oxide scavenger L-NNA, guanylate cyclase antagonist methylene blue and pyrogallol, soluble guanylate cyclase inhibitor ODQ on the icariin induced relaxation effects of CC smooth muscle strips.

| Concentration | $10^{-6}$ M | $10^{-5}$ M | $10^{-4}$ M | p value |
|---|---|---|---|---|
| Control (n = 8) | 1.23 ± 0.82% | 4.42 ± 1.08% | 23.12 ± 1.36% | <0.01 |
| L-NNA (N = 5) | 0.82 ± 0.58% | 3.23 ± 0.89% | 15.68 ± 1.15% | <0.01 |
| Methylene blue (n = 5) | 0.52 ± 0.68% | 2.02 ± 0.45% | 13.45 ± 1.12% | <0.01 |
| Pyrogallol (n = 5) | 0.85 ± 0.45% | 3.45 ± 0.73% | 15.68 ± 1.15% | <0.01 |
| ODQ (n = 5) | 0.42 ± 0.48% | 1.85 ± 0.35% | 10.45 ± 1.08% | <0.01 |
| P value | <0.01 | <0.01 | <0.01 | |

With these results we conclude that Icariin has the relaxation effects on CC smooth muscle to enhancing sexual function, and the other components showed no significant effects on corpus cavernosum at all. The pharmaceutical mechanism of the relaxation effect of icariin was activating NO-cGMP signaling pathway to enhancing penile erection.

EXPERIMENT 5

Effects of Intracavernous Adminitration of Icariin on Intracavernosal Press(ICP) and Systimatic Mean Atrerial Press(MAP) Changes in Rats In order to further understand the effects of Icariin on penile erection, we investigated the effects of icariin on intracavernosal press(ICP) and systimatic mean arterial pressure (MAP) changes by electrically stimulated the cavernous nerve (CN) of adult male rat in vivo study. An vasodilator reserpin as the controls.

Twenty-four male, adult Wistar rats(weight:300–350 g) were used. After anesthetization, the left carotid artery was cannulated to monitor mean arterial pressure (MAP). Bipolar electrodes were positioned on the cavernous nerve (CN); the right cavernous body was cannulated with 26 G needle connected with Biopack MP100 to monitor ICP changes. After intracavemosal administration of 100 μl different concentration Icariin or Reserpine ($10^{-8}$M to $10^{-4}$M) respectively, the CN was electrically stimulated (ES) 10 minutes later and ICP and MAP were monitored. In order to investigate the possible mechanism of the effect of icariin on ICP changes, 100 µl different concentration guanylate cyclase inhibitor ODQ ($10^{-8}$M-$10^{-4}$M) were intracavemosal administrated 10 minutes after Icariin (100 µl $10^{-4}$M) administration into CC, and then the ICP was measured during erection, which was, followed the ES.

In the results, icariin significantly increased ICP in a dose-dependent manner (Table 3). However, icariin had no obviously influence on the rat's MPA. The effects of icariin increasing ICP were significantly inhibited by different concentration of ODQ(Table 4). However, reserpine decreased both of MAP and ICP in a concentration dependent manner(p<0.01). (Table 5)

With these results we conclude that Icariin can increase the ICP in a dose-dependent manner for enhancing sexual function without significantly influenced on MAP. The mechanism of icariin increasing ICP may be mediated by activation of NO-cGMP signaling pathway important molecular guanylate cyclase activity and it is a potential drug for treating erectile dysfunction. Reserpine, however, have been showed the inhibiting effects on both of MAP and ICP, which may have the inhibiting effect by sexual function because of decreasing ICP and MAP.

TABLE 3

Increasing ICP effects of Icariin on rat induced by CN stimulation.

| Icariin conc. | $10^{-7}$M | $10^{-6}$M | $10^{-5}$M | $10^{-4}$M | P value |
|---|---|---|---|---|---|
| Increase ICP (%) | 5.53 ± 0.69 | 10.82 ± 1.06 | 30.48 ± 3.06 | 58.01 ± 5.78 | <0.01 |

TABLE 4

Inhibiting effects of ODQ on Icariin induced ICP changes of rat induced by CN stimulation

| ODQ conc. | $10^{-7}$M | $10^{-6}$M | $10^{-5}$M | $10^{-4}$M | P value |
|---|---|---|---|---|---|
| Inhibiting Effect on Icariin induced Relaxation of CC. (%) | 17.16 ± 1.77 | 23.09 ± 4.29 | 58.45 ± 6.00 | 80.24 ± 8.05 | <0.01 |

TABLE 5

Inhibiting effects of Reserpine on ICP and MAP changes of rat induced by CN stimulation.

| Reserpine conc. | $10^{-7}$M | $10^{-6}$M | $10^{-5}$M | $10^{-4}$M | P value |
|---|---|---|---|---|---|
| Inhibiting Effect on MAP (%) | 3.97 ± 1.24 | 8.36 ± 2.26 | 17.57 ± 3.37 | 19.81 ± 3.57 | <0.01 |
| Inhibiting effects on ICP (%) | 4.81 ± 1.35 | 17.39 ± 3.45 | 33.34 ± 4.28 | 59.63 ± 5.39 | <0.001 |

EXPERIMENT 6

Effects of Icariin on cGMP/cAMP Formation in Corpus Cavernosum of Rabbit

Icariin($C_{33}H40O_{15}$;W/M 676.67) is a falavonoid isolated from natural drug *Epimedii herba*, which shown to have the a dose related relaxation effects on CC smooth muscle and have the inhibiting effects on PDE5. We investigated the effects of icariin on cGMP/cAMP formation in CC of penis for realizing the effect of icariin on male sexual function influenced by cGMP level changes and on systematic blood press changes influenced by cAMP level changes.

Male New Zealand White rabbits(2.5 kg) were killed and penis were rapidly excised and cut into segments and incubated with various concentrations of Icariin or Sildenafil. Formation of cGMP/cAMP was stimulated with sodium nitroprusside(SNP) and the $^{125}$I cGMP/cAMP concentrations measured by radioimmunoassay procedure.

In the results, In the presence of SNP, Icariin increased cGMP concentrations in rabbit corpus cavemosum in a dose dependent manner(p<0.001). The cGMP concentration changes by Icariin $10^{-6}$M:8.66±2.03 fmol/mg·min, $10^{-5}$M:8.92±1.67 fmol/mg·min☐ $10^{-4}$M: 10.82±1.58 fmol/mg·min☐ $10^{-3}$M:10.43±1.49 fmol/mg·min; Sildenafil $10^{-6}$M:10.65±2.28 fmol/mg·min, $10^{-5}$M:12.69±2.24 fmol/mg·min☐ $10^{-4}$M: 11.98±2.39fmol/mg·min☐ $10^{-3}$M:12.35±2.56 fmol/mg·min☐ Papaverine $10^{-6}$M: 8.66±2.07fmol/mg·min, $10^{-5}$M:8.92±1.87 fmol/mg·min☐ $10^{-4}$M: 9.82±2.16 fmol/mg·min☐ $10^{-3}$M:11.43±65 fmol/mg·min☐ EC50 of icariin, Sildenafil and papaverine were 5.13 µM, 0.31 µM, 3.15 µM, respectively.

With these results we concluded that the relaxation effect of icariin on corpus cavemosum was mediated by increasing cGMP levels by inhibiting effects of PDE5 to activation of NO-cGMP signaling pathway. However, no significantly influenced by cAMP levels this result may indicate that icariin have no significant influence on systematic blood press changes.

EXPERIMENT 7

Effects of Icariin on the Activities of cGMP Specific PDE5 and cAMP Specific PDE4

Icariin, which is a flavenoid isolated from *Epimedii herba*, have shown to have the relaxation effects on the CC smooth muscle by increasing cGMP levels in previous study. In order to understand the mechanism of Icariin on NO-cGMP signaling pathway, the inhibiting effects of icariin on the activities of cAMP specific PDE4, which may regulation of systematic blood press, and cGMP specific PDE5, which plays the important role of regulation of sexual function, were investigated.

PDE5 and PDE4 were isolated from human platelets and liver tissue using a Pharmacia FPLC system and Mono Q column. The cyclic nucleotide PDE5/PDE4 activities in FPLC fractions were determined using a modification of the two-step radioisotope procedure ([$^3$H]GMP/[$^3$H]AMP). In studies of the kinetics of inhibitions of PDE5/PDE4 by Icariin(papaverine and Sildenafil as the controls), [$^3$H]-cGMP and [$^3$H]AMP substrate concentrations ranged from 0.3 µM to 10 µM were used and initial rates of hydrolysis were determined in the absence or the presence of samples.

In the results, the inhibition effects of Icariin, papaverine and Sildenafil on PDE5 isolated from human platelets showed in a dose dependent manner, and the $IC_{50}$ of Icariin PDE5 was 0.432 $\mu M$, papaverine 0.680 $\mu M$ and Sildenafil 0.004 $\mu M$, respectively. The inhibition effects of Icariin, papaverine and sildenafil on PDE4 isolated from human liver tissue showed in a dose dependent manner, and the $IC_{50}$ of icariin on PDE4 was 73.50 $\mu M$, papaverine 3.07 $\mu M$ and Sildenafil 14.58 $\mu M$, respectively. These results indicated that Icariin have the more specific inhibition effects on PDE5 compared to PDE4(170.14 times), however, the inhibiting potency of Icariin on PDE5 was no statistically different compared to papaverine, however it was significantly weaker than that of Sildenafil(108.10 times).

With these results we conclude that Icariin have the selective inhibiting effect on cGMP specific PDE5 compared to cAMP specific PDE4, and icariin is a new PDE5 inhibitor and it may increase cGMP levels of CC smooth muscle for enhancing penile erection, therefore may do not significantly influence on cAMP mediated systematic blood press.

EXPERIMENT 8

Expression of PDE5 and Effectis of Icariin on cGMP Formation in Rabbit CC of Clitoris Icariin(C331H40O15;W/M 676.67) is a falavonoid isolated from natural drug *Epimedii herba*, which shown to have the a dose related relaxation effects on CC smooth muscle and have the inhibiting effects on PDE5. We investigated the expression of PDE5 in CC of clitoris tissue and the effects of Icariin on the in vitro formation of cGMP, which is the most important molecular in the regulation of sexual function, in the clitoris CC of rabbit for realizing Icariin on female sexual function.

Female New Zealand White rabbits(2.5 kg) were killed and clitoris rapidly excised and cut into segments. One of which was used to extract RNA followed by RT-PCR to detect the expression of PDE5, others were incubated with various concentrations of Icariin or Sildenafil. Formation of cGMP was stimulated with sodium nitroprusside(SNP) and the $^{125}I$ cGMP concentrations measured by radioimmunoassay procedure.

In the results, there was a lane around 800 bp on the agar electrophoresis of the production of RT-PCR□ which was as long as we designed according to CDNA sequence of PDE5. Icariin and Sildenafil significantly increased cGMP concentration in clitoris CC of female rabbits. $EC_{50}$ of Icariin and Sildenafil were 3.16 $\mu M$ and 0.31 $\mu M$ respectively.

With these results we conclude that PDE5 is presented in CC of clitoris tissue and clitoris cavemosum relaxation response may mediate by NO-cGMP signaling pathway also. The mechanism of Sildenafil and Icariin on clitoris erection may involve the activation of the NO-cGMP signal pathway by inhibiting effect on cGMP specific PDE5 activity to increase cGMP levels.

EXPERIMENT 9

The Effect of Icariin on the Expretion of NOS Isoform mRNAexpressions After Long-term Oral Administration in Castrated Sexual Dysfunction Model of Rat To determine the effect of long-term oral administration of icariin which isolated from *Epimedii herba* on the mRNA expression of NOS isoforms using immuohistochemical stain and molecular biologic method of RT-PCR procedure, which plays the important role of regulation of sexual function, in castrated ED animal model to elucidate the mechanism of Icariin on elevating sexual activity.

Male Wistar rats(300–350 g)(n=24) randomly divide into 4 Groups; Group A for control; Group B for castrated and administration normal saline; Group C for castrated and oral administration Icariin (mg/kg); Group D for castrated and oral administration Icariin (5 mg/kg) for 3 months. After observe mating behavior, the animal was killed, the penis was excised rapidly, and cut into four parts. One of them used for immuohistochemical stain, the others was socked into RNAlater and stored in −70 condition. nNOS, eNOS, iNOS mRNA were semi-quantified by RT-PCR, β-actin as a controls. Specificity of RT-PCR products was confirmed by sequencing procedure, with-assay and between-assay variation was carried out respectively.

In Group A all rats observed sexual activities, however□ 66.7%(n=4/6) of rats in Group B lost the sexual activities. Among of Group C and D, 83.3% (n=10/12) castrated rats restored sexual activities. According to results of immuohistochemic stain, the expression of nNOS and iNOS were decreased in Group B compared Group A, however, expressed in Group C and Group D. The results of RT-PCR showed that nNOS, eNOS and iNOS mRNA expressed in Group A, however, in Group B iNOS and nNOS mRNA showed decreased expression. In Group C and D, the nNOS and iNOS mRNA were significantly increased compared to control Group B($p<0.05$). However, eNOS mRNA in all castrated rats was not expressed. (Table 6, 7)

Icariin can increase nNOS and iNOS expression in castrated rat model after long-term oral administration. These results implied that Icariin may have a long-term therapeutic effect on sexual dysfunction. However, all castrated rats did not expressed eNOS, which may relate to epithelial cell of corpus cavernosum apoptosis after castration, further study is needed.

TABLE 6

Effects of icariin on iNOS mRNA expressions after long-term oral administration different concentration of icariin on castrated rat model by RT-PCR analysis.

| Groups | Mean conc./area (β-actin) | Mean conc./area (iNOS) | Ratio (iNOS/β-actin) |
|---|---|---|---|
| Group A | 25.92 | 28.80 | 0.90 |
| Group B | 46.40 | 12.96 | 0.28 |
| Group C | 34.56 | 17.28 | 0.50* |
| Group D | 31.36 | 23.20 | 0.74* |

*$p < 0.05$

TABLE 7

Effects of icariin on nNOS mRNA expressions after long-term oral administration different concentration of icariin on castrated rat model by RT-PCR analysis.

| Groups | Mean conc./area (β-actin) | Mean conc./area (nNOS) | Ratio (nNOS/β-actin) |
|---|---|---|---|
| Group A | 20.50 | 32.50 | 1.59 |
| Group B | 16.50 | 11.00 | 0.67 |

TABLE 7-continued

Effects of icariin on nNOS mRNA expressions after long-term oral administration different concentration of icariin on castrated rat model by RT-PCR analysis.

| Groups | Mean conc./area (β-actin) | Mean conc./area (nNOS) | Ratio (nNOS/β-actin) |
|---|---|---|---|
| Group C | 36.60 | 44.60 | 0.82* |
| Group D | 38.80 | 36.40 | 1.08* |

*p < 0.05

EXPERIMENT 10

Effects of Icariin on Patients with Sexual Dysfunction; A Pilot Placebo Controlled Clinical Study In order to understand the clinical efficacy of icariin, the effects of icariin on patients with sexual dysfunction was investigated with an international index of erectile dysfunction(IIEF5) which was used for evaluating sexual function clinically.

This clinical test was conducted for 56 patients suffer from sexual dysfunction and who agreed to this clinical study of icariin using an IIEF5 symptom score which was used for evaluating sexual function. The mean age of the patients was 36±6.7 years. The subjects included 7 diabetic patients(25%), 6 hypertension patients(21.4%), and 5 cardiac-vascular disease patient(17.9%). The patients were randomly classified into two groups, one group for Icariin another group for placebo and had no information on the drugs used. The test drug (icariin 50 mg/tablets, 2 tablets/dose, 3 times/day) and placebo were administered to patients for one month. Prior to administering drugs, sexual functions of all patients were evaluated by using IIEF5. After administering drugs, sexual function changes of the patients were re-evaluated by using the IIEF5. The comparison and analysis of the results were carried out.

Before administration, IIEF5 score were shown that confidence on penile erection and maintenance of erection (No 1) was 1.87±0.54, erection ability to interpose penis into vagina(No 2) was 1.89±0.67, the ability to maintain erection after vaginal penetration during their sexual intercourse (No 3)was 1.82±0.65, and the inability to maintain erection and maintenance of erection during their sexual intercourse (No 4) was 1.89±0.61,and satisfaction with their sexual lives(No 5)was 1.79±0.62, respectively. Most of patients suffer from mild to moderate sexual dysfunction.

After administration of icariin one month, the IIEF5 score were shown that confidence on penile erection and maintenance of erection(No 1) was 3.32±0.39 for icariin tablet, 2.04±0.63 for control drug. The erection ability to interpose penis is penetrated into vaginal during intercourse(No 2) 3.11±0.32 for icariin tablet, and 2.05±0.88 for control drug, the ability to maintain erection after vaginal penetration during their sexual intercourse (No 3) was 3.18±0.47 for icariin tablet, and 2.17±0.97 for control drug, and inability to maintain erection and maintains erection during sexual intercourse (No 4) was 3.25±0.47 for icariin tablet, and 2.18±0.92 for control drug, and satisfaction with sexual lives (No 5) was 3.36±0.47 for icariin tablet, and 2.14±0.95 for control drug. These results proven that icariin significantly improved sexual function compared to placebo($p<0.01$.

TABLE 8

Effects of icariin tablet on patients with sexual dysfunction evaluated by IIEF5

| IIEF5 | No 1 | | No 2 | | No 3 | | No 4 | | No 5 | |
|---|---|---|---|---|---|---|---|---|---|---|
| | Pre Tx | Post Tx | Pre Tx | Post Tx | Pre Tx | Post Tx | Pre Tx | Post Tx | Pre Tx | Post Tx |
| Icariin tablet (n = 26) | 1.82 ± 0.54 | 3.32 ± 0.39 | 1.89 ± 0.67 | 3.11 ± 0.32 | 1.82 ± 0.65 | 3.18 ± 0.47 | 1.89 ± 0.61 | 3.25 ± 0.47 | 1.79 ± 0.62 | 3.36 ± 0.47 |
| placebo (n = 26) | 1.82 ± 0.54 | 2.04 ± 0.63 | 1.89 ± 0.67 | 2.07 ± 0.88 | 1.82 ± 0.65 | 2.17 ± 0.97 | 1.89 ± 0.61 | 2.18 ± 0.92 | 1.79 ± 0.62 | 2.14 ± 0.95 |
| P value | | 0.002 | | 0.001 | | 0.001 | | 0.002 | | 0.001 |

The overall clinical effectiveness was 75.4% for icariin tablet and 35.4% for placebo. There were no significant side effects expect that 4 patient show a mild gastric reaction. There were not observed significant differences in clinical efficacy and side effects between diabetic, hypertension and cardiac problem patients.

It is apparent from the results of the above teat that icariin has the relaxation effects on corpus cavernosum smooth muscle. NO-cGMP pathway as well as inhibition of PDE5 enzyme to increase the concentration of cGMP mediates the mechanism of icariin on corpus cavernosum smooth muscle. It is implied that icariin may enhance penile erection during sexual arousal in man with erectile dysfunction.

As set above, icariin as a new cGMP specific PDE5 inhibitor has a relaxation effect on corpus cavemosal smooth muscle to improve a sexual function as well as has the relaxation effect on clitoris CC smooth muscle and no significantly influence on systematic blood press changes. Further, it has a long-term effect in the treatment of sexual dysfunction. Therefore, icariin or the pharmaceutical composition containing icariin of the present invention can be effectively and safely used as a medical agent for preventing and treating a male and female sexual dysfunction.

I claim:

1. A method of treating erectile dysfunction of a warm blooded animal consisting essentially of orally administrating to said warm blooded animal an effective amount of icariin as a single and purified compound.

2. The method according to claim 1, wherein the effective amount of icariin is 1–500 mg.

3. The method according to claim 1, wherein said pharmaceutical composition is in a dosage form selected from the group consisting of tablets, pills, suspensions, capsules, chewing gums and granules.

\* \* \* \* \*